(12) United States Patent
Bavouzet et al.

(10) Patent No.: US 8,679,777 B2
(45) Date of Patent: Mar. 25, 2014

(54) YEAST STRAINS FOR THE PRODUCTION OF ALCOHOL

(75) Inventors: Jean-Michel Bavouzet, Croix (FR); Jean-Marc Ladriere, Querenaing (FR); Annie Tbaikhi, Wambrechies (FR); William Wyme, Marquette (FR)

(73) Assignee: Lesaffre et Compagnie, Paris (FR)

( * ) Notice: Subject to any disclaimer, the term of this patent is extended or adjusted under 35 U.S.C. 154(b) by 0 days.

(21) Appl. No.: 13/515,902

(22) PCT Filed: Dec. 14, 2010

(86) PCT No.: PCT/FR2010/000834
§ 371 (c)(1),
(2), (4) Date: Jun. 14, 2012

(87) PCT Pub. No.: WO2011/080411
PCT Pub. Date: Jul. 7, 2011

(65) Prior Publication Data
US 2012/0252061 A1    Oct. 4, 2012

(30) Foreign Application Priority Data

Dec. 15, 2009  (FR) ...................................... 09 06049

(51) Int. Cl.
*C12Q 1/04* (2006.01)
*C12P 7/02* (2006.01)

(52) U.S. Cl.
USPC ............................................ 435/34; 435/155

(58) Field of Classification Search
USPC .................................................. 435/34, 155
See application file for complete search history.

(56) References Cited

U.S. PATENT DOCUMENTS

| 2011/0129901 A1* | 6/2011 | Fuentes et al. ................. 435/247 |
| 2011/0165612 A1* | 7/2011 | Colavizza et al. .............. 435/29 |
| 2013/0040353 A1* | 2/2013 | Desfougeres et al. ........ 435/161 |

FOREIGN PATENT DOCUMENTS

WO    WO 2009 137804 A1    11/2009

OTHER PUBLICATIONS

Delgenes et al., Effects of lignocellulose degradation products on ethanol fermentation of glucose and xylose by *Saccharomyces cerevisiae*, *Zymomonas mobilis*, *Pichia stipites*, and *Candida shehatae*; vol. 19, Issue 3, Aug. 15, 1996, pp. 220-225.*
International Search Report received in PCT/FR2010/000834.
Almeida, J., et al., "Increased Tolerance and Conversion of Inhibitors in Lignocellulosic Hydrolysates by *Saccharomyces cerevisiae*", Journal of Chemical Technology and Biotechnology, Blackwell Scientific Publications, vol. 82, No. 4, Apr. 1, 2007, pp. 340-349.
Kadar, Z., et al., "Ethanol Fermentation of Various Pretreated and Hydrolyzed Substrates at Low Initial pH", Applied Biochemistry and Biotechnology, vol. 137, Apr. 2007, pp. 847-858.
Ness, F., et al., "RTM1: A Member of a New Family of Telomeric Repeated Genes in Yeast", Genetics, vol. 140, No. 3, 1995, pp. 945-956.

* cited by examiner

*Primary Examiner* — Karen Cochrane Carlson
*Assistant Examiner* — Jennifer M Tichy
(74) *Attorney, Agent, or Firm* — Vedder Price P.C.; Thomas J. Kowalski; Deborah L. Lu (57) ABSTRACT

The present invention relates to novel yeast strains intended for alcohol production.
The present invention also relates to yeasts obtained by cultures of said yeast strains and use thereof for producing alcohol, in particular in a toxic fermentation medium.
Another object of the invention relates to a method of selecting yeast strains that are resistant to a toxic fermentation medium.

6 Claims, 5 Drawing Sheets

YEAST STRAINS FOR THE PRODUCTION OF ALCOHOL

RELATED APPLICATIONS

The present application is filed pursuant to 35 U.S.C. §371 as a U.S. National Phase application of International Patent Application No. PCT/FR2010/000834, which was filed on Dec. 14, 2010, claiming the benefit of priority to French Patent Application No. FR 09 06049 filed on Dec. 15, 2009. The entire content of each of the aforementioned applications is incorporated herein by reference in its entirety.

FIELD OF TECHNOLOGY

The present invention relates to novel yeast strains and yeasts derived from these novel strains intended for producing alcohol in toxic media, a method of selecting said strains, as well as a method of producing alcohol, notably in toxic media.

TECHNOLOGICAL BACKGROUND

For an industrial undertaking it is advantageous to recycle the liquor resulting from fermentations with a view to using it in a new fermentation medium. Among other things, this makes it possible to reduce the amounts of water entering and leaving the fermenters.

Traditionally, the liquor is recycled after fermentation on media containing sources of sugars obtained from beet or cane, such as LS2 media (*Lean Syrup from the 2nd crystallization of sugar*), but also after fermentation on media containing sugars derived from wheat or maize. The recycled liquor can supply nutritional elements for the yeast, but in particular it has a certain toxicity for the yeast, and this toxicity will increase as the degree of recycling increases.

Moreover, certain raw materials used in the fermentation media are in themselves toxic to yeast. This is the case for example with molasses (also called LS3, or *Lean Syrup from the 3rd crystallization of sugar*).

The toxicity of the recycled liquor and of these toxic raw materials results notably from the presence of organic acids and salts.

In a toxic medium containing, partially or completely, recycled liquor and/or toxic raw materials, the known yeasts used in alcoholic fermentation have a kinetics of alcohol production slower than in a non-toxic medium. Moreover, the maximum amount of alcohol produced by the known yeasts in fermentation in a toxic medium is lower than in a non-toxic medium.

When the raw materials used are toxic in themselves, dilution of them in the fermentation medium makes it possible to limit their toxic effect. However, this dilution causes very large additional costs, connected notably with lower volume-based productivity and higher costs of cooling and distillation.

Attempts to solve the problem of toxic media have until now focused on making the fermentation medium less toxic. However, no really satisfactory solution has been found for this problem.

There is therefore a real need to provide an alternative solution for improving alcohol production by yeasts in toxic fermentation media.

"Improvement of alcohol production" means an improvement of the kinetics of alcohol production in a toxic fermentation medium, while maintaining an acceptable quantity of alcohol produced.

SUMMARY OF THE INVENTION

A first object of the invention is to provide a strain of *Saccharomyces cerevisiae* selected from the strain deposited at the CNCM under number I-4264, the strain deposited at the CNCM under number I-4265, the strain deposited at the CNCM under number I-4411 and the strain deposited at the CNCM under number I-4412.

A second object of the invention relates to a method of selecting a yeast strain resistant to a toxic medium, comprising:
  a step of fermentation of at least one yeast strain in a toxic selective medium and in a non-toxic selective medium,
  the initial composition of the toxic selective medium being the initial composition of the non-toxic selective medium with addition of at least one non-ionized organic acid at a toxic concentration and
  sugar being the limiting factor of the fermentation in the toxic selective medium and in the non-toxic selective medium, and
  a step of selection of at least one yeast strain for which the amount of alcohol produced at time $t_{max}$ in the toxic selective medium is greater than or equal to 65% of the amount of alcohol produced at time $t_{max}$ by said strain in the non-toxic selective medium.

A third object of the invention is a strain that can be obtained by the method as defined above.

A fourth object of the invention is a strain of *Saccharomyces cerevisiae* derived from a strain as defined above.

A fifth object of the invention is a yeast obtained by culture of a yeast strain as defined above.

A sixth object of the invention relates to the use of a yeast as defined above for producing alcohol.

A seventh object of the invention is a method of producing alcohol comprising a step of fermentation of at least one yeast as defined above, in a fermentation medium.

BRIEF DESCRIPTION OF THE DRAWINGS

The maximum amount of alcohol produced (in g/kg of initial medium) is shown on the ordinate for each of the hybrids 1 to 13 tested (abscissa). "T" corresponds to the reference strain I-4071.

The ordinate shows the amount of alcohol produced at time $t_{max}$ in a toxic selective medium as a percentage of the amount of alcohol produced at time $t_{max}$ in a non-toxic selective medium.

The abscissa shows the hybrids tested (1, 2, 8 and 11).

The ordinate shows the weight loss (in g/kg of initial medium) and the abscissa shows the time in hours.

The reference strain I-4071 is represented by the dotted curve with black diamonds, the yeast strain I-4264 (hybrid 1) by the curve with triangles, the yeast strain I-4265 (hybrid 2) by the curve with squares, hybrid 8 by the curve with circles and hybrid 11 by the curve with grey diamonds.

The ordinate shows the weight loss (in g/kg of initial medium) and the abscissa shows the time in hours.

The reference strain I-4071 is represented by the dotted curve with black diamonds, the yeast strain I-4264 (hybrid 1) by the curve with triangles, the yeast strain I-4265 (hybrid 2) by the curve with squares, hybrid 8 by the curve with circles and hybrid 11 by the curve with grey diamonds.

The ordinate shows the weight loss (in g/kg of initial medium) and the abscissa shows the time in hours.

The reference strain I-4071 is represented by the dotted curve with black diamonds, the yeast strain I-4264 by the curve with triangles and the yeast strain I-4265 by the curve with squares.

The ordinate shows the weight loss (in g/kg of initial medium) and the abscissa shows the time in hours.

The reference strain I-4071 is represented by the dotted curve with black diamonds, the yeast strain I-4264 by the curve with triangles and the yeast strain I-4265 by the curve with squares.

The ordinate shows the weight loss (in g/kg of initial medium) and the abscissa shows the time in hours.

The reference strain I-4071 is represented by the dotted curve with black diamonds, the yeast strain I-4264 by the curve with triangles and the yeast strain I-4265 by the curve with squares.

The ordinate shows the weight loss (in g/kg of initial medium) and the abscissa shows the time in hours.

The reference strain I-4071 is represented by the dotted curve with black diamonds, the yeast strain I-4264 by the curve with triangles and the yeast strain I-4265 by the curve with squares.

The ordinate shows the weight loss (in g/100 g of initial medium) and the abscissa shows the time in hours.

The reference strain I-4071 is represented by the dotted curve with black diamonds, the yeast strain I-4411 by the curve with triangles and the yeast strain I-4412 by the curve with squares.

DETAILED DESCRIPTION OF THE INVENTION

The inventors have elaborated an original alternative solution for improving alcohol production by yeasts in toxic fermentation media. This alternative solution consists of selecting new yeast strains that are resistant to a toxic fermentation medium by means of an original method of strain selection.

Thus, when we have a yeast strain that is resistant to a toxic fermentation medium, a yeast is obtained that is resistant to a toxic fermentation medium.

A toxic fermentation medium according to the invention is a fermentation medium that comprises at least one stress factor.

A stress factor is for example stress connected with the presence of organic acids, stress connected with the presence of salts, stress connected with the presence of other inhibitory organic molecules, or stress connected with osmotic pressure.

"Other inhibitory organic molecules" means for example aromatic benzene and furan compounds.

A preferred stress factor according to the invention is the presence of at least one non-ionized organic acid at a toxic total concentration.

The expression "total concentration" denotes the concentration corresponding to all the non-ionized organic acids present in the fermentation medium.

An "non-ionized organic acid" or "organic acid in non-ionized form" is a carboxylic acid in its protonated form.

A toxic concentration of non-ionized organic acid(s) can be defined relative to its toxic effect on alcohol production of a reference yeast strain.

A reference yeast strain for production of alcohol is the *Saccharomyces cerevisiae* strain deposited by the Applicant on Sep. 4, 2008 at the CNCM (National Collection of Cultures of Microorganisms, Institut Pasteur, 25 rue du Docteur Roux, 75724 Paris Cedex 15, France) under number I-4071.

In order to evaluate the toxicity of a given concentration of non-ionized organic acid(s), we compare:

the amount of alcohol produced by the reference strain I-4071, measured at time $t_{max}$, in a limiting sugar fermentation medium containing the non-ionized organic acid or acids, and the amount of alcohol produced by said reference strain, measured at time $t_{max}$, in a fermentation medium of the same composition, except that essentially it does not comprise any non-ionized organic acid.

A toxic concentration of non-ionized organic acid(s) is then for example a concentration leading to a decrease in the amount of alcohol produced at time $t_{max}$ by yeast strain number I-4071 by 25% to 75% relative to the maximum amount of alcohol produced by said strain at time $t_{max}$ in a medium of the same composition but essentially not comprising non-ionized organic acid, preferably a decrease by 40% to 75%.

Said "fermentation medium containing the non-ionized organic acid or acids" is called toxic selective medium hereinafter.

Said "fermentation medium of the same composition except that essentially it does not comprise any non-ionized organic acid" is called non-toxic selective medium hereinafter.

The non-toxic selective medium comprises all the nutrients necessary to permit cell growth of at least 5 g of dry yeast equivalent per kg of medium.

The "time $t_{max}$" denotes the moment when the maximum amount of alcohol produced by a yeast strain is reached in a non-toxic selective medium.

The alcoholic fermentation curve showing the amount of alcohol produced as a function of time generally comprises three phases:

a lag phase, during which there is no production of ethanol, a phase of alcohol production, and a plateau phase, which corresponds to the end of fermentation.

The maximum amount of alcohol produced corresponds to the amount of alcohol produced when the plateau phase of alcoholic fermentation is reached.

The terms "alcohol" and "ethanol" will be used indiscriminately hereinafter.

The expressions "sugar-limiting" or "sugar being the limiting factor of the fermentation" signify that fermentation stops when the fermentable sugars are completely consumed in the fermentation medium.

The expressions "non-sugar-limiting" or "sugar not being the limiting factor of fermentation" signify that fermentation stops but the fermentable sugars have not been completely consumed in the fermentation medium.

A medium that essentially does not comprise non-ionized organic acids is a medium in which the amount of alcohol produced by yeast strain number I-4071 is not altered significantly for the entire duration of fermentation relative to the amount of alcohol produced by said strain in a medium of the same composition, except that it does not contain any non-ionized organic acid.

For example, a medium comprising a concentration less than or equal to 100 mM of citric acid at a pH from 4.5 to 5.5 is a medium essentially not comprising organic acid in non-ionized form.

The expression "yeast strain" denotes a relatively homogeneous population of yeast cells.

A yeast strain is obtained by isolating a clone, a clone being a population of cells obtained from a single yeast cell.

A yeast strain according to the invention is preferably a yeast strain that has not been genetically modified.

"Yeast strain resistant to a toxic medium" denotes a yeast strain whose kinetics of alcohol production is not slowed excessively in a toxic fermentation medium.

Preferably, a yeast strain resistant to a toxic medium has kinetics of alcohol production that is slowed less than that of a conventional strain intended for producing alcohol, for example such as the yeast strain deposited at the CNCM under number I-4071.

In order to select novel yeast strains resistant to a toxic medium, the inventors elaborated an original new method of selecting yeast strains. Application of this method made it possible in particular to obtain the 2 novel strains of *Saccharomyces cerevisiae* deposited on 2 Dec. 2009 by virtue of the Budapest Treaty at the CNCM (*National Collection of Cultures of Microorganisms, Institut Pasteur*, 25 *rue du Docteur Roux*, 75724 Paris Cedex 15, France) under numbers I-4264 and I-4265.

Usually, when evaluating yeast strains intended for alcohol production, the criterion used for selection is the maximum amount of alcohol produced at the end of fermentation.

The novel original method of selecting yeast strains resistant to a toxic medium uses the kinetics of alcohol production as the selection criterion.

Thus, the method of selection according to the invention comprises a step of selecting yeast strains based on their kinetics of alcohol production in a sugar-limiting toxic selective medium relative to their kinetics of alcohol production in a sugar-limiting non-toxic selective medium.

In a preferred embodiment of the invention, the method of selection comprises an additional step of selecting yeast strains based on their kinetics of alcohol production in a sugar-limiting toxic selective medium relative to the kinetics of alcohol production of a reference yeast strain in this same toxic selective medium.

In another preferred embodiment, the method of selection according to the invention comprises an additional step of selecting yeast strains based on their maximum amount of alcohol produced in a non-sugar-limiting non-toxic selective medium relative to the maximum amount of alcohol produced by a reference yeast strain in the same non-toxic selective medium.

When the method comprises one or both additional selection steps, the different selection steps are carried out in any order.

In an advantageous embodiment, the method of selection comprises the two additional selection steps as defined below.

The method of selection according to the invention can further comprise a prior step of obtaining yeast strains by crossing and/or mutagenesis.

The present invention thus relates to a method of selecting a yeast strain resistant to a toxic medium, comprising:
a step of fermentation of at least one yeast strain in a toxic selective medium and in a non-toxic selective medium, the initial composition of the toxic selective medium being the initial composition of the non-toxic selective medium with addition of at least one non-ionized organic acid at a toxic concentration and sugar being the limiting factor of the fermentation in the toxic selective medium and in the non-toxic selective medium, and
a step of selection of at least one yeast strain for which the amount of alcohol produced at time $t_{max}$ in the toxic selective medium is greater than or equal to 65% of the amount of alcohol produced at time $t_{max}$ by said strain in the non-toxic selective medium.

"Initial composition" denotes the composition of the selective medium when fermentation begins.

When the selective medium comprises more than one non-ionized organic acid, the toxic concentration is the total toxic concentration of non-ionized organic acids.

By providing "sugar-limiting" conditions, this ensures that conditions are favourable for evaluating the kinetics of alcohol production, connected without bias with the tolerance of the strain to alcohol and connected without bias with the initial osmotic pressure connected with the sugars.

The fermentation is carried out in the absence of aeration.

The fermentation is preferably carried out with stirring.

The initial pH of the toxic and non-toxic selective media is identical.

The pH of the toxic and non-toxic selective media is such that it does not inhibit the metabolism of the yeast strain.

For example, the pH of the toxic and non-toxic selective media is above 3.5 throughout fermentation.

In an advantageous embodiment of the method of selection, the fermentation step is carried out at constant pH.

The seeding of the selective medium is identical in the toxic selective medium and in the non-toxic selective medium.

Preferably, seeding is slight, so as not to favour yeast strains on the toxic selective medium, on account of the seeding.

The seeding is for example from 0.100 g to 0.200 g of cells of the yeast strain (in dry matter equivalent) per kg of medium.

The fermentation of the yeast strain is generally carried out at a temperature from 28° C. to 37° C., preferably from 30° C. to 33° C.

Preferably, fermentation of the yeast strain is carried out at a temperature of 32° C.

In a preferred embodiment of the method of selection, the toxic selective medium and the non-toxic selective medium do not contain pentoses, lignocellulosic substrate, cereal hydrolysate or wort, aromatic benzene compounds, aromatic furan compounds and/or molasses.

In a preferred embodiment of the method of selection, the presence of at least one non-ionized organic acid at a toxic total concentration is the only stress factor in the toxic selective medium used.

In particular, in a preferred embodiment of the method of selection, the toxic and non-toxic selective media do not have stress connected with the presence of salts, stress connected with the presence of other inhibitory organic molecules and/or stress connected with osmotic pressure.

The amount of alcohol produced is measured by any suitable means known by a person skilled in the art.

It can be direct measurement of the alcohol produced or indirect measurement via a parameter correlated with the production of alcohol.

For example, alcohol production can be measured by chromatography, notably by HPLC (high-performance liquid chromatography), GC (gas chromatography), densimetry, enzymatic kit (for example ethanol assay kit from Boehringer-Mannheim R-Biopharm, Cat No. 10 176 290 035) or analysis with potassium dichromate.

The production of alcohol can also be measured indirectly in an alcoholic fermentation test by measurement of weight loss.

The time $t_{max}$ is the moment when the maximum amount of alcohol produced by said yeast strain is reached in said non-toxic selective medium.

The present invention relates in particular to a method of selection as defined above, characterized in that it comprises:
- a step of fermentation of at least one yeast strain in a toxic selective medium and in a non-toxic selective medium, the initial composition of the toxic selective medium being the initial composition of the non-toxic selective medium with addition of at least one non-ionized organic acid at a toxic concentration and sugar being the limiting factor of the fermentation in the toxic selective medium and in the non-toxic selective medium, and
- a step of selection of at least one yeast strain for which the amount of alcohol produced at time $t_{max}$ in the toxic selective medium is greater than or equal to 70%, preferably greater than or equal to 75% of the amount of alcohol produced at time $t_{max}$ by said strain in the non-toxic selective medium.

The present invention preferably relates to a method as defined above, characterized in that the toxic selective medium and the non-toxic selective medium are synthetic media.

A synthetic medium is a medium whose exact chemical composition is known.

A synthetic medium according to the invention comprises a single source of carbon, a source of nitrogen, a source of phosphorus, as well as the vitamins and minerals that are essential for growth of a yeast strain.

The source of carbon of the synthetic medium is a fermentable sugar, preferably a sugar supplied in the form of glucose or sucrose.

The sources of nitrogen and of phosphorus are for example supplied by DAP (Di-Ammonium Phosphate or $(NH_4)_2HPO_4$).

The synthetic medium can be buffered at a given pH, preferably at a pH above 3.5. For example, the synthetic medium can comprise citric acid as buffer.

As an exception to the definition of a synthetic medium, the synthetic medium according to the invention can comprise a yeast extract.

Suitable synthetic media for application of the method of selection according to the invention are for example the sugar-limiting, toxic and non-toxic selective media described in example 1.

The present invention relates more particularly to a method as defined above, characterized in that the non-ionized organic acid is selected from acetic acid, lactic acid, formic acid, levulinic acid or a mixture thereof.

In a preferred embodiment, the present invention relates to a method of selection as defined above, characterized in that the non-ionized organic acid is acetic acid.

In a preferred embodiment of the invention, the method of selection also comprises a step of selecting yeast strains based on their kinetics of alcohol production in the toxic selective medium relative to the kinetics of alcohol production of a reference yeast strain in this same toxic selective medium.

The present invention thus relates to a method as defined above, characterized in that it comprises an additional step of selection of at least one yeast strain for which the amount of alcohol produced at time $t_{max\ ref}$ in said toxic selective medium is greater than the amount of alcohol produced at time $t_{max\ ref}$ by yeast strain number I-4071 in said same toxic selective medium.

The time $t_{max\ ref}$ is the time $t_{max}$ of the reference strain I-4071, i.e. the moment when the maximum amount of alcohol produced by reference strain I-4071 is reached in the non-toxic selective medium.

The toxic selective medium and the non-toxic selective medium are as defined above, in particular the toxic and non-toxic selective media are in sugar-limiting conditions.

The amount of alcohol produced at time $t_{max\ ref}$ in said toxic selective medium by the selected yeast strain is increased preferably by at least 15%, preferably by at least 20%, more preferably at least 25% relative to the amount of alcohol produced at time $t_{max\ ref}$ by yeast strain number I-4071 in said same toxic selective medium.

In another preferred embodiment, the method of selection according to the invention comprises an additional step of selecting yeast strains based on their maximum amount of alcohol produced in a non-sugar-limiting non-toxic selective medium relative to the maximum amount of alcohol produced by a reference yeast strain in the same non-toxic selective medium.

In order to compare the yeast strains on the basis of their maximum amount of alcohol produced, sugar is not then the limiting factor of fermentation.

In this case, it is the concentration of alcohol in the non-toxic selective medium that becomes the limiting factor of fermentation.

The higher the amount of alcohol produced at the end of fermentation, the more the yeast strain is tolerant to alcohol.

The present invention thus relates to a method as defined above, characterized in that it comprises an additional step of selection, in a non-toxic selective medium in which sugar is not the limiting factor of fermentation, of at least one yeast strain for which the maximum amount of alcohol produced is greater than or equal to 90% of that of strain number I-4071, preferably greater than or equal to 92% of that of strain number I-407 in said same non-toxic selective medium.

The method according to the invention advantageously comprises the three selection steps as defined above.

The details of an example of a method of selection according to the invention are given in example 1.

Surprisingly and unexpectedly, the method of selecting resistant strains according to the invention made it possible to obtain yeast strains that are resistant to a toxic medium, which have both improved kinetics of alcohol production in a toxic medium, and a high maximum amount of alcohol produced in a non-sugar-limiting non-toxic medium.

Now, yeast strains generally have either good kinetics of alcohol production in a toxic medium, or a high maximum amount of alcohol produced in a non-sugar-limiting non-toxic medium, one of these two parameters being improved to the detriment of the other.

The present invention relates to a method as defined above, characterized in that it comprises a prior step of obtaining yeast strains by crossing and/or mutagenesis.

The crossing of yeast strains is performed according to conventional techniques, such as those taught in chapter 7 "Sporulation and Hybridization of Yeast" by R. R. Fowell, in the reference work "The Yeasts", Volume 1, editors A. H. Rose and J. S. Harrison, 1969—Academic Press.

A conventional crossing technique comprises:
a step of sporulation of yeasts to obtain segregants,
an optional step of selection of the segregants from at least one of the two parents based on the maximum amount of alcohol produced, and
a step of crossing the segregants, to obtain hybrids.

The hybrids constitute new yeast strains used for selecting yeast strains resistant to a toxic medium.

The term "mutagenesis" denotes both conventional mutagenesis obtained by radiation or by mutagenic chemicals and insertional mutagenesis by transposition or by integration of an exogenous DNA fragment.

Mutagenesis by radiation comprises the use of UV, X, or gamma radiation.

The mutagenic chemicals are for example EMS (ethyl-methyl sulphonate), EES (ethyl-ethyl sulphonate), nitrosoguanidine, nitrous acid, aflatoxin B1, hydroxylamine, 5-bromouracil, 2-aminopurine, proflavin, acridine orange.

In an advantageous embodiment, the step of obtaining yeast strains comprises a step of conventional mutagenesis, optionally followed by enrichment, for example in a toxic medium.

The resistance of yeast strains I-4264 and I-4265 according to the invention was verified in a toxic synthetic medium displaying stronger toxicity associated with acetic acid (5 g/kg at pH 4.5) and moreover displaying toxicity associated with alcohol, owing to the fact that sugar is not the limiting factor of fermentation.

Sugar is then preferably supplied in the form of dextrin to avoid sugar-related osmotic stress.

Figure 4:
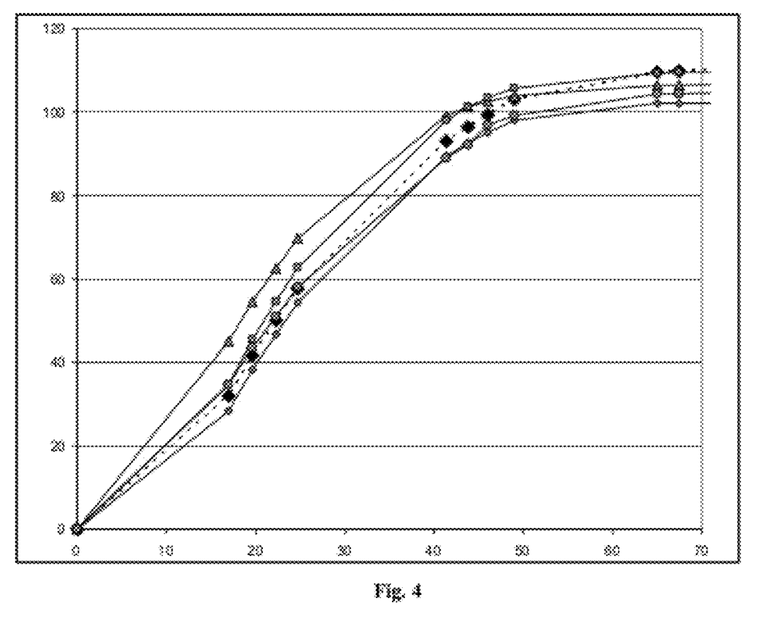
FIG. 4: Kinetics of alcohol production in fermentation in a toxic synthetic application medium (5 g/kg of acetate at pH 4.5, sugar fermentation non-limiting)

Yeast strains I-4264 and I-4265 showed a kinetic advantage relative to the reference yeast strain I-4071 in this toxic synthetic medium (cf. example 1 and FIG. 4).

Surprisingly and unexpectedly, the method of selection according to the invention makes it possible to obtain yeast strains with quicker kinetics of alcohol production than the reference strain number I-4071 in a toxic industrial application medium comprising several stress factors, including at least one non-ionized organic acid at a toxic concentration.

Figure 6:
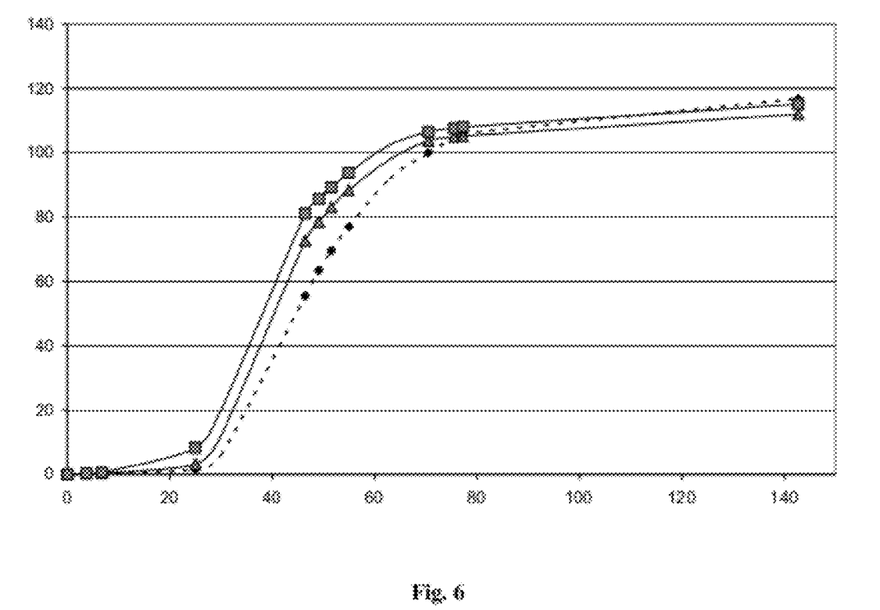
FIG. 6: Kinetics of alcohol production in fermentation in a toxic application medium B containing vinasse (sugar fermentation non-limiting)
Figure 7:
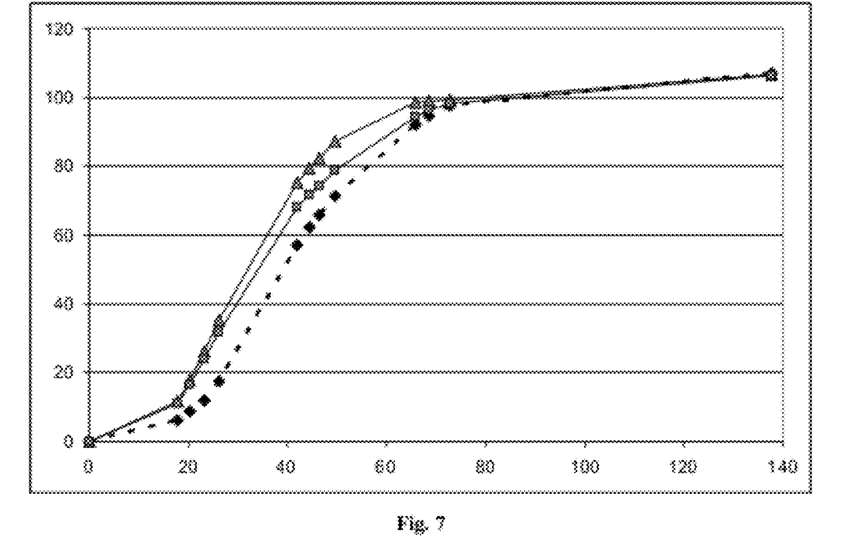
FIG. 7: Kinetics of alcohol production in fermentation in a toxic application medium C containing slightly diluted beet molasses (sugar fermentation non-limiting)
Figure 8:
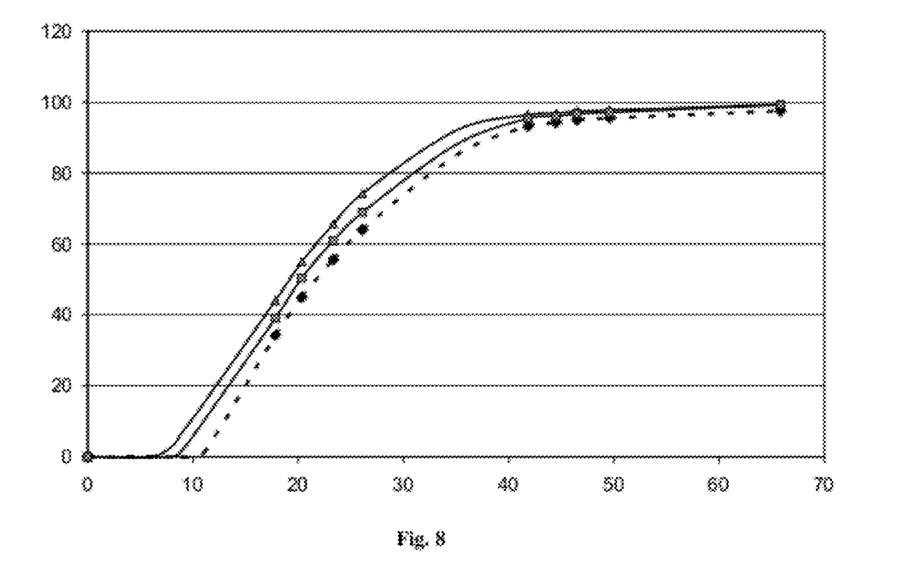
FIG. 8: Kinetics of alcohol production in fermentation in a toxic application medium D containing slightly diluted cane molasses (sugar fermentation non-limiting)

Thus, yeast strains I-4264 and I-4265 according to the invention have quicker kinetics of alcohol production than the reference yeast strain I-4071 in toxic fermentation media containing vinasse (see example 2 and FIGS. 5 and 6) and in toxic fermentation media containing slightly diluted molasses (see example 2 and FIGS. 7 and 8).

Yeast strains I-4264 and I-4265 therefore offer a real industrial advantage in the application of alcoholic fermentations in toxic media.

In fact, the quicker kinetics of alcohol production makes it possible to obtain a higher volume-based hourly productivity of the fermentation vats.

Moreover, another advantage of the yeast strains according to the invention is the reduction in duration of the lag phase during fermentation in a toxic medium, which limits the contamination of the medium with other microorganisms.

A toxic fermentation medium is for example a medium containing 9% to 11% of non-sugars (relative to the total dry matter of the medium), the non-sugars being supplied for example by vinasse and/or molasses.

"Vinasse" denotes the wastewater from distillation of alcoholic liquids.

The "non-sugars" comprise mineral salts, the organic molecules that are not consumed during fermentation and the organic molecules produced during fermentation.

The present invention also relates to a yeast strain obtained or obtainable by the method as defined above.

The yeast strain obtained or obtainable by the method as defined above is preferably a yeast strain that has not been genetically modified.

The present invention also relates to all the strains derived from the yeast strains that are resistant to a toxic medium according to the invention and that share the same properties.

A yeast strain resistant to a toxic medium according to the invention is more particularly a strain intended for the production of yeasts used in distilling and/or in winemaking and/or in brewing and/or for the production of fermented beverages and/or for producing industrial alcohol intended for example for biofuels or for the chemical industries.

A yeast strain resistant to a toxic medium according to the invention is preferably a strain of *Saccharomyces*, notably a strain of *Saccharomyces cerevisiae*.

The present invention thus relates to a strain of Saccharomyces cerevisiae selected from the strain deposited at the CNCM under number I-4264 and the strain deposited at the CNCM under number I-4265.

Yeast strain I-4264 was obtained by crossing yeast strains.

Yeast strain I-4264 produces an amount of alcohol at time $t_{max}$ in a toxic selective medium greater than or equal to 90% of the amount of alcohol produced at time $t_{max}$ by said strain in a non-toxic selective medium, the initial composition of said toxic selective medium being the initial composition of the non-toxic selective medium with addition of at least one non-ionized organic acid at a toxic concentration and sugar being the limiting factor of the fermentation in the toxic selective medium and in the non-toxic selective medium (cf. example 1).

Yeast strain I-4264 produces an amount of alcohol at time $t_{max\ ref}$ in said toxic selective medium that is increased by at least 50% relative to the amount of alcohol produced at time $t_{max\ ref}$ by yeast strain number I-4071 in said same toxic selective medium (cf. example 1).

Yeast strain I-4264 produces a maximum amount of alcohol in a non-sugar-limiting non-toxic selective medium greater than or equal to 92% of that of strain number I-4071 in said same non-toxic selective medium (cf. example 1).

Yeast strain I-4265 was obtained by crossing yeast strains.

Yeast strain I-4265 produces an amount of alcohol at time $t_{max}$ in a toxic selective medium greater than or equal to 75% of the amount of alcohol produced at time $t_{max}$ by said strain in a non-toxic selective medium, the initial composition of said toxic selective medium being the initial composition of the non-toxic selective medium with addition of at least one non-ionized organic acid at a toxic concentration and sugar being the limiting factor of the fermentation in the toxic selective medium and in the non-toxic selective medium (cf. example 1).

Yeast strain I-4265 produces an amount of alcohol at time $t_{max\ ref}$ in said toxic selective medium that is increased by at least 25% relative to the amount of alcohol produced at time $t_{max\ ref}$ by yeast strain number I-4071 in said same toxic selective medium (cf. example 1).

Yeast strain I-4265 produces a maximum amount of alcohol in a non-sugar-limiting non-toxic selective medium greater than or equal to 92% of that of strain number I-4071 in said same non-toxic selective medium (cf. example 1).

The present invention therefore relates to the two strains described above and all of the strains belonging to the same family, in particular all the derived strains that share the same properties as these two strains.

The present invention thus relates to a yeast strain derived from a strain according to the invention as defined above, characterized in that the amount of alcohol produced by said derived strain at time $t_{max}$ in a toxic selective medium is greater than or equal to 65% of the amount of alcohol produced at time $t_{max}$ by said strain in a non-toxic selective medium, the initial composition of the toxic selective medium being the initial composition of the non-toxic selective medium with addition of at least one non-ionized organic acid at a toxic concentration, and sugar being the limiting factor of the fermentation in the toxic selective medium and in the non-toxic selective medium.

The present invention also relates to a derived strain of Saccharomyces cerevisiae as defined above, characterized in that its amount of alcohol produced at time $t_{max\ ref}$ in said toxic selective medium is greater than the amount of alcohol produced at time $t_{max\ ref}$ by yeast strain number I-4071 in said same toxic selective medium.

The present invention also relates to a derived strain of Saccharomyces cerevisiae as defined above, characterized in that in a non-toxic selective medium in which sugar is not the limiting factor of fermentation, its maximum amount of alcohol produced is greater than or equal to 90% of that of strain number I-4071 in said same non-toxic selective medium.

The expression "derived strain" denotes a strain derived by any transformation whatsoever, for example one or more crossings and/or one or more mutations and/or one or more genetic transformations.

A strain derived by crossing can be obtained by crossing a strain according to the invention with the same strain, or another strain according to the invention, or any other strain.

A strain derived by mutation can be a strain that has undergone at least one spontaneous mutation in its genome or at least one induced mutation, for example by mutagenesis.

The mutation or mutations of the derived strain may or may not be silent.

A strain derived by genetic transformation is a strain in which exogenous DNA has been introduced.

Said exogenous DNA can be supplied by a plasmid.

Said exogenous DNA is preferably integrated in the yeast genome.

A derived strain can also be a clone isolated from a culture of a yeast strain according to the invention.

The present invention thus relates to the strains of Saccharomyces cerevisiae deposited on 8 Dec. 2010 by virtue of the Budapest Treaty at the CNCM (*National Collection of Cultures of Microorganisms, Institut Pasteur,* 25 *rue du Docteur Roux,* 75724 *Paris Cedex* 15, *France*) under numbers I-4411 and I-4412.

Yeast strain I-4411 was obtained by isolation of a clone from a culture of strain I-4264.

Yeast strain I-4411 produces an amount of alcohol at time $t_{max}$ in a toxic selective medium greater than or equal to 95% of the amount of alcohol produced at time $t_{max}$ by said strain in a non-toxic selective medium, the initial composition of said toxic selective medium being the initial composition of the non-toxic selective medium with addition of at least one non-ionized organic acid at a toxic concentration and sugar being the limiting factor of the fermentation in the toxic selective medium and in the non-toxic selective medium (cf. example 1).

Surprisingly, the kinetics of alcohol production of yeast strain I-4411 is not altered in a toxic selective medium relative to the non-toxic selective medium.

Yeast strain I-4411 produces an amount of alcohol at time $t_{max\ ref}$ in said toxic selective medium that is increased by at least 12% relative to the amount of alcohol produced at time $t_{max\ ref}$ by yeast strain number I-4071 in said same toxic selective medium (cf. example 1).

Yeast strain I-4411 produces a maximum amount of alcohol in a non-sugar-limiting non-toxic selective medium greater than or equal to 95% of that of strain number I-4071 in said same non-toxic selective medium (cf. example 1).

Yeast strain I-4412 was obtained by isolation of a clone from a culture of strain I-4264.

Yeast strain I-4412 produces an amount of alcohol at time $t_{max}$ in a toxic selective medium greater than or equal to 72% of the amount of alcohol produced at time $t_{max}$ by said strain in a non-toxic selective medium, the initial composition of said toxic selective medium being the initial composition of the non-toxic selective medium with addition of at least one non-ionized organic acid at a toxic concentration and sugar being the limiting factor of the fermentation in the toxic selective medium and in the non-toxic selective medium (cf. example 1).

Yeast strain I-4412 produces an amount of alcohol at time $t_{max\ ref}$ in said toxic selective medium greater than or equal to 90% of the amount of alcohol produced at time $t_{max\ ref}$ by yeast strain number I-4071 in said same toxic selective medium (cf. example 1).

Yeast strain I-4412 produces a maximum amount of alcohol in a non-sugar-limiting non-toxic selective medium greater than or equal to 95% of that of strain number I-4071 in said same non-toxic selective medium (cf. example 1).

Figure 9:
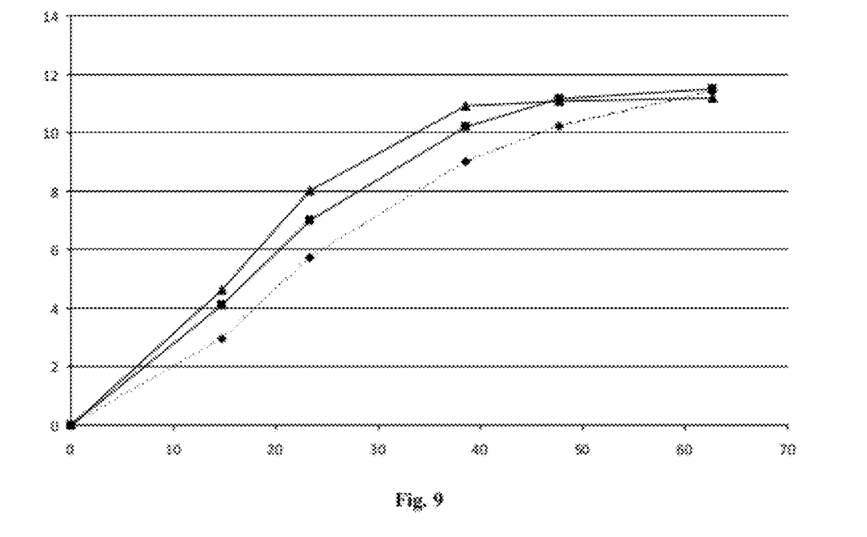
FIG. 9: Kinetics of alcohol production in fermentation in a toxic application medium E containing vinasse (sugar fermentation non-limiting)

Moreover, yeast strains I-4411 and I-4412 have quicker kinetics of alcohol production than the reference yeast strain I-4071 in toxic fermentation media containing vinasse (see example 2 and FIG. 9).

Yeast strains I-4411 and I-4412 therefore offer a real industrial advantage in the application of alcoholic fermentations in toxic media.

The invention also relates to a method of transformation of a yeast strain that is resistant to a toxic medium, to obtain a derived strain as defined above, said method of transformation comprising a step of transformation of said strain by at least one crossing and/or at least one mutation and/or at least one genetic transformation.

The present invention relates in particular to a yeast obtained by culture of a yeast strain as defined above.

The yeasts according to the invention are particularly interesting in the following applications:

- so-called "potable" alcohol, intended for the manufacture of alcoholic beverages, and/or
- industrial alcohol, intended for example for biofuels or for chemical industries.

The yeasts are produced from yeast strains resistant to a toxic medium according to the invention, notably as described in the reference book "Yeast Technology", 2nd edition, 1991, G. Reed and T. W. Nagodawithana, published by Van Nostrand Reinhold, ISBN 0-442-31892-8.

The multiplication of yeasts, on an industrial scale, generally comprises at least the first two steps of the following set of steps:

multiplication of a yeast strain in several stages, firstly in semi-anaerobiosis, then in aerobiosis, separation of the yeast thus produced from its culture medium by centrifugation, to obtain a liquid yeast cream containing between about 12 and 25% of dry matter, or an even larger amount of dry matter if the yeast cream is mixed with osmolyte products, filtration of the liquid yeast cream thus obtained, generally on a rotary filter under vacuum, to obtain a dehydrated fresh yeast containing 26% to 35% of dry matter, mixing of said dehydrated fresh yeast, to obtain a homogeneous mass, extrusion of the yeast thus obtained, to obtain
- a compressed yeast in the form of fresh yeast or crumbled fresh yeast blocks, containing about 30% of dry matter, or
- a yeast in the form of particles, generally granules, if the yeast is intended to be dried, optionally, controlled drying, in a hot air stream, for example by fluidization, of the yeast particles obtained by extrusion, to obtain dry yeast.

The drying step is preferably controlled rapid drying in the presence of an emulsifier.

Among the emulsifiers that can be used in the drying step, sorbitan monostearate can be selected, used for example at a concentration of about 1.0% (by weight relative to the weight of dry yeast).

The yeasts according to the invention are yeasts that are resistant to a toxic medium.

The yeasts according to the invention can be used in any possible form.

For example, the present invention relates to a yeast as defined above, characterized in that it is in the form of yeast cream, compressed yeast, dry yeast or frozen yeast.

The present invention also relates to the use of a yeast as defined above for producing alcohol.

The production of alcohol is obtained by alcoholic fermentation.

The conditions of alcoholic fermentation depend on the type of application required, for example depending on whether it is a fermentation of the brewing, winemaking or distillery type.

A person skilled in the art is able to determine the appropriate conditions for alcoholic fermentation.

The alcoholic fermentation medium comprises the following elements: at least one fermentable carbon source, at least one source of nitrogen, at least one source of sulphur, at least one source of phosphorus, at least one source of vitamins and/or at least one source of minerals.

The source of carbon is for example supplied in the form of a sugar that can be assimilated immediately by the yeast, glycerol, ethanol and/or a mixture thereof.

The source of carbon is preferably a sugar that can be assimilated immediately by the yeast, for example a simple sugar such as glucose or fructose, or a disaccharide of the sucrose type and/or a mixture of these sugars.

The sugar can be supplied in the form of glucose syrups and/or fructose syrups and/or starch hydrolysates and/or in the form of molasses and/or in the form of LS2 (*Lean Syrup from the 2nd crystallization of sugar*) and/or in the form of a substance capable of giving sugars that can be assimilated by the yeast strain and/or in the form of a mixture thereof.

The source of nitrogen is for example supplied in the form of ammonium sulphate, ammonium hydroxide, diammonium phosphate, ammonia, urea and/or a combination thereof.

The source of sulphur is for example supplied in the form of ammonium sulphate, magnesium sulphate, sulphuric acid and/or a combination thereof.

The source of phosphorus is for example supplied in the form of phosphoric acid, potassium phosphate, diammonium phosphate, mono-ammonium phosphate, and/or a combination thereof.

The source of vitamins is for example supplied in the form of molasses, yeast hydrolysate, solution of pure vitamin or of a mixture of pure vitamins and/or a combination thereof.

The source of vitamins supplies the yeast with all of the vitamins in amounts at least equivalent to those recommended in the reference works. Several sources of vitamins can be combined.

The source of minerals is for example supplied in the form of molasses, a mixture of mineral salts and/or a combination thereof.

The source of minerals supplies the yeast with all of the macroelements and trace elements in amounts at least equivalent to those recommended in the reference works. Several sources of minerals can be combined.

One and the same substance can supply several different elements.

As an example, reference may be made to the conditions of alcoholic fermentation described in the reference book "Yeast Technology", 2nd edition, 1991, G. Reed and T. W. Nagodawithana, published by Van Nostrand Reinhold, ISBN 0-442-31892-8.

The present invention preferably relates to the use of a yeast as defined above for producing alcohol in a toxic fermentation medium.

The present invention also relates to a method of producing alcohol comprising a step of fermentation of at least one yeast according to the invention as defined above, in a fermentation medium.

The fermentation medium is as defined above.

The present invention relates in particular to a method of producing alcohol as defined above, characterized in that said fermentation medium is a toxic fermentation medium.

The present invention relates more particularly to a method of producing alcohol as defined above, characterized in that said toxic fermentation medium comprises recycled water and/or molasses.

The recycled water is for example vinasse, a grain steep liquor, flegmass, water from condensation of fermentation gases, or water obtained from the concentration of vinasse.

The percentage of recycled water, vinasse and/or molasses in the toxic fermentation medium depends on the fermentation conditions.

The fermentation medium comprises for example from 20% to 40% of vinasse.

The present invention relates in particular to a method of producing alcohol as defined above, comprising a step of partial or total recycling of the fermentation medium.

The fermentation medium can be recycled continuously or at different time intervals during fermentation.

In a continuous process for alcohol production with a cascade of fermenters, the fermentation medium can be recycled in the first fermentation vat or vats.

The present invention will now be illustrated by means of the following examples, which are given for illustration and are not in any way limiting.

The examples describe in particular a method of selecting yeast strains according to the invention that are resistant to a toxic medium, and their characteristics.

Example 1

Selection of Yeast Strains Resistant to a Toxic Medium

Materials and Methods
1. Media

| YEG Medium | |
|---|---|
| Glucose | 20 g |
| Yeast extract | 5 g |
| Agar | 30 g |
| Water | q.s. 1 l |

| Toxic selective medium (sugar-limited) | | Non-toxic selective medium (sugar-limited) | |
|---|---|---|---|
| Glucose | 150 g | Glucose | 150 g |
| Yeast extract | 5 g | Yeast extract | 5 g |
| $(NH_4)_2HPO_4$ | 4.70 | $(NH_4)_2HPO_4$ | 4.70 |
| Acetic acid | 2.52 g | Citric acid | 11.40 g |
| Sodium acetate | 2.08 g | Sodium citrate | 13.50 g |
| Citric acid | 11.40 g | Vitamins | |
| Sodium citrate | 13.50 g | Mineral salts | |
| Vitamins | | Water | q.s. 1 kg |
| Mineral salts | | pH 4.5 | |
| Water | q.s. 1 kg | | |
| pH 4.5 | | | |

| Toxic synthetic application medium (not sugar-limited) | | Non-toxic selective medium (not sugar-limited) | |
|---|---|---|---|
| Dextrin | 307.3 g | Glucose | 300 g |
| Yeast extract | 5 g | Yeast extract | 5 g |
| $KH_2PO_4$ | 1 g | $KH_2PO_4$ | 1 g |
| Urea | 2.5 g | Urea | 2.5 g |
| Citric acid | 0.36 g | Citric acid | 0.36 g |
| Citrate | 0.53 g | Citrate | 0.53 g |
| Acetic acid | 5 g | Acetic acid | 2.50 g |
| Vitamins | | Vitamins | |
| Mineral salts | | Mineral salts | |
| Water | q.s. 1 kg | Water | q.s. 1 kg |
| pH 4.5 | | pH 5.5 | |

| Preculture medium | | Sporulation medium | |
|---|---|---|---|
| Sucrose | 100 g | Sodium acetate | 6.5 g |
| Yeast extract | 20 g | Agar | 15 g |
| Mineral salts | | Water | q.s. 1 l |
| Water | q.s. 1 l | pH 6.5 | |

+ amyloglucosidase added extemporaneously

All the media used are sterilized.

2. Crossing for Obtaining Hybrids

The yeast strains are sporulated on the sporulation medium for 3 to 5 days at 30° C. The yeast cells are recovered in sterile water. They are then digested with β-glucanase prepared extemporaneously at 20 mg/ml, for 30 min, at 30° C. and with stirring.

The yeast cells are then spread on a YEG agar medium. The spores are then dissected using a micromanipulator. The spores are cultured at 30° C. for 2 days.

The spores of the parent strains are mixed on YEG agar medium. Hybridization is carried out for 3 to 5 days at 30° C. The mixtures are then spread on YEG agar medium. After incubation for 48 h at 30° C., colonies appear and PCR is carried out on these colonies in order to identify the hybrids (Huxley et al., 1990).

3. Fermentation

The yeast cells are precultured in 10 ml of preculture medium adjusted to pH 4.7 for 24 h at 30° C.

2 ml of this preculture is inoculated in 200 ml of preculture medium for 20 h at 26° C. with stirring.

The yeast cells are then recovered by centrifugation for 5 min at 4500 rpm and at 4° C. The yeast cells are washed with cold water and are centrifuged again in the same conditions. The yeast cells are recovered in 40 ml of cold water.

The dry matter obtained is measured.

Fermentation is carried out at 32° C., in the absence of aeration, with stirring (95 rpm).

The fermentation medium (toxic selective medium or non-toxic selective medium) is seeded at 0.125 g of yeasts (in dry matter equivalent) per kg of medium.

4. Measurement of the Amount of Alcohol Produced—Direct Method

The amount of ethanol is determined by high-performance liquid chromatography (HPLC) (Shimadzu®) using an Aminex HPX 87H column (Biorad®), proton exchanger resin, eluted with 5 mM sulphuric acid solution.

5. Evaluation of the Amount of Alcohol Produced—Indirect Method

As the amount of alcohol produced is correlated with the weight loss of the fermentation medium, the amount of alcohol produced is evaluated from the weight loss of the fermentation medium. After calculation, the amount of alcohol produced is obtained (in g/kg of initial medium).

Results

1. Crossing

Several yeast strains from the applicant's culture collection are used as parent strains for the crossings.

2. Preselection of Hybrids Based on the Maximum Amount of Alcohol Produced in a Non-Toxic Selective Medium Out of the hybrids obtained in the crossing step, 59 hybrids are then tested on the basis of the maximum concentration of alcohol produced in a non-toxic selective medium, in conditions where sugar is non-limiting.

Figure 1:
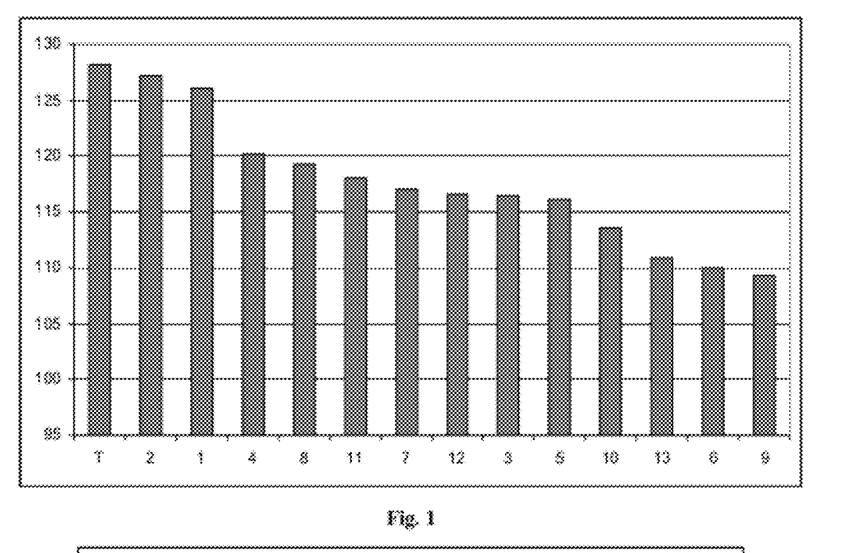
FIG. 1: Maximum amount of alcohol produced at the end of fermentation in a non-toxic selective medium (sugar fermentation non-limiting)

FIG. 1 shows the amount of alcohol produced in the non-toxic selective medium (in g/kg) at the end of fermentation for the 13 best hybrids.

The final amount of alcohol produced by the hybrids is compared with that of the reference strain I-4071 (designated T in FIG. 1).

The hybrids for which the maximum amount of alcohol produced is greater than or equal to 92% of that of reference strain I-4071 are preselected. They are hybrids 1, 2, 4, 8 and 11.

3. Selection of Hybrids Based on their Kinetics of Alcohol Production in a Toxic Selective Medium Relative to a Non-Toxic Selective Medium Hybrids 1, 2, 4, and 8 are then tested on the basis of their kinetics of alcohol production in the toxic selective medium relative to the non-toxic selective medium.

Figure 2:
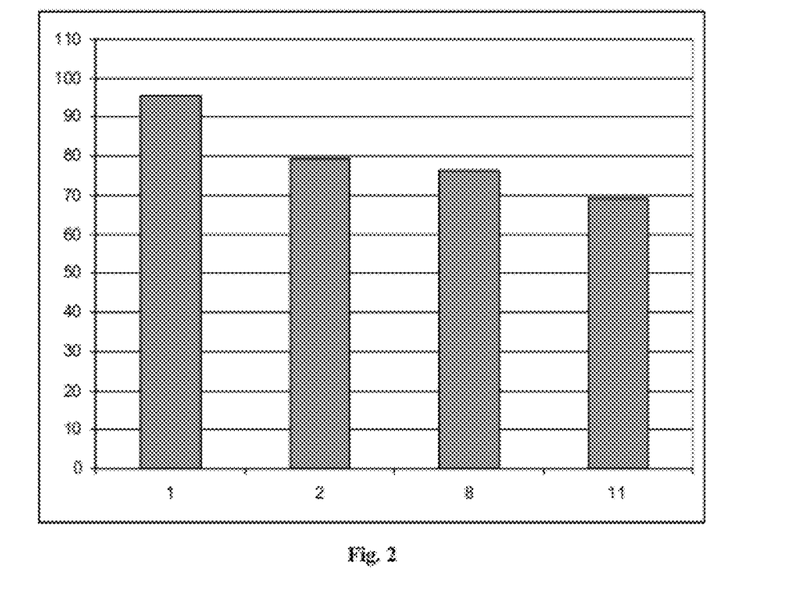
FIG. 2: Effect of a toxic selective medium on the amount of alcohol produced at time $t_{max}$ (sugar fermentation limiting)

The results are presented in FIG. 2 for hybrids 1, 2, 8 and 11.

As hybrid 4 has a problem with growth on the toxic selective medium, it is not shown in FIG. 2.

At its time $t_{max}$, hybrid 1 produces an amount of alcohol in the toxic selective medium that is greater than or equal to 90% of the amount of alcohol produced in the non-toxic selective medium.

At its time $t_{max}$, hybrid 2 produces an amount of alcohol in the toxic selective medium that is greater than or equal to 75% of the amount of alcohol produced in the non-toxic selective medium.

At its time $t_{max}$, hybrid 8 produces an amount of alcohol in the toxic selective medium that is greater than or equal to 70% of the amount of alcohol produced in the non-toxic selective medium.

At its time $t_{max}$, hybrid 11 produces an amount of alcohol in the toxic selective medium that is greater than or equal to 65% of the amount of alcohol produced in the non-toxic selective medium.

For comparison, at its time $t_{max}$, the reference yeast strain I-4071 produces an amount of alcohol in the selective medium equal to 60% of the amount of alcohol produced in the non-toxic selective medium.

Hybrids 1, 2, 8 and 11 are selected during this step.

4. Selection of Hybrids Based on their Kinetics of Alcohol Production in a Toxic Selective Medium Relative to the Reference Strain I-4071

Hybrids 1, 2, 8 and 11 are then tested in fermentation in the toxic selective medium relative to the reference yeast strain I-4071.

Figure 3:
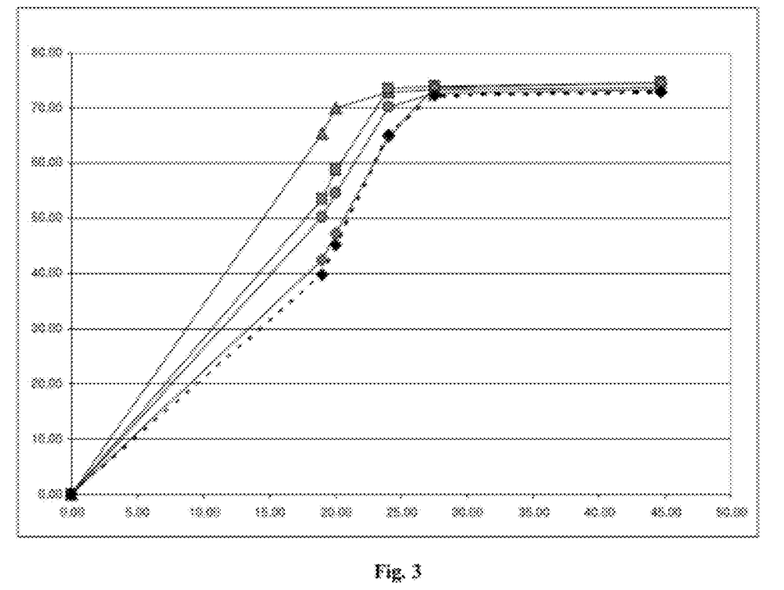
FIG. 3: Kinetics of alcohol production in fermentation in a toxic synthetic selective medium (3.6 g/kg of acetate at pH 4.5, sugar fermentation limiting)

FIG. 3 shows that the kinetics of alcohol production of hybrids 1, 2 and 8 is quicker than that of strain I-4071.

The kinetics of alcohol production of hybrid 11 is close to that of the reference strain I-4071.

Moreover, hybrid 1 produces an amount of alcohol at time $t_{max\ ref}$ in the toxic selective medium that is increased by at least 50% relative to the amount of alcohol produced at time $t_{max\ ref}$ by yeast strain number I-4071 in this toxic selective medium.

Regarding hybrid 2, it produces an amount of alcohol at time $t_{max\ ref}$ in the toxic selective medium that is increased by at least 25% relative to the amount of alcohol produced at time $t_{max\ ref}$ by yeast strain number I-4071 in this toxic selective medium.

Regarding hybrid 8, it produces an amount of alcohol at time $t_{max\ ref}$ in the toxic selective medium that is increased by at least 20% relative to the amount of alcohol produced at time $t_{max\ ref}$ by yeast strain number I-4071 in this toxic selective medium.

The resistance of hybrids 1, 2, 8 and 11 is then tested in the toxic synthetic application medium, which has higher toxicity connected with acetic acid (5 g/kg at pH 4.5) and moreover has toxicity connected with the alcohol, because the sugar is added in an amount that does not limit the fermentation.

The sugar is supplied in the form of dextrins to avoid sugar-related osmotic stress.

As shown in FIG. 4, only yeast strains I-4264 and I-4265 showed a kinetic advantage relative to the reference yeast strain I-4071 in this toxic synthetic application medium.

In conclusion, hybrids 1 and 2 have a kinetic advantage relative to the reference strain I-4071 during production of alcohol in the toxic synthetic selective medium. Hybrids 1 and 2 correspond respectively to yeast strains I-4264 and I-4265 according to the invention.

5. Isolation of Clones from a Culture of Yeast Strain I-4264

A culture of yeast strain I-4264 is grown in YEG medium.

The culture is then spread on a dish. Several clones are selected and their kinetics of alcohol production is evaluated, as well as the maximum amount of alcohol produced in the non-sugar-limiting non-toxic selective medium.

The results obtained relating to clones A and C are shown in Table 1.

TABLE 1

| Clone | Amount of alcohol produced at $t_{max}$ in the toxic medium/ non-toxic medium (sugar-limited) | Amount of alcohol produced relative to strain I-4071 at $t_{max\ ref}$ in the toxic medium (sugar-limited) | Maximum amount of alcohol produced in the non-toxic selective medium relative to strain I-4071 (not sugar-limited) |
|---|---|---|---|
| Clone A | 99% | +15% | 98.6% |
| Clone C | 76% | −10% | 98.7% |

Clones A and C have a maximum amount of alcohol produced greater than or equal to 95% of that of reference strain I-4071 in a non-toxic selective medium, in conditions that are not sugar-limited.

At its time $t_{max}$, clone A produces an amount of alcohol in the toxic selective medium that is greater than or equal to 95% of the amount of alcohol produced in the non-toxic selective medium (sugar-limiting).

At its time $t_{max}$, clone C produces an amount of alcohol in the toxic selective medium that is greater than or equal to 72% of the amount of alcohol produced in the non-toxic selective medium (sugar-limiting).

The clones are then evaluated in fermentation in the toxic selective medium (sugar-limiting) relative to the reference yeast strain I-4071.

The kinetics of alcohol production of clone A is quicker than that of strain I-4071. Clone A thus produces an amount of alcohol at time $t_{max\ ref}$ in the toxic selective medium that is increased by at least 12% relative to the amount of alcohol produced at time $t_{max\ ref}$ by yeast strain number I-4071 in this toxic selective medium.

Clone A displays a real kinetic advantage relative to the reference strain I-4071 during production of alcohol in the toxic synthetic selective medium.

The kinetics of alcohol production of clone C is slightly lower relative to that of the reference strain I-4071.

Clone C produces an amount of alcohol at time $t_{max\ ref}$ in the toxic selective medium greater than or equal to 90% of the amount of alcohol produced at time $t_{max\ ref}$ by yeast strain number I-4071 in this toxic selective medium.

Clones A and C correspond respectively to yeast strains I-4411 and I-4412.

Example 2

Use of the Yeast Strains According to the Invention in a Toxic Application Medium Materials and Methods 1. Media

| Medium A | | Medium B | |
|---|---|---|---|
| LS2 from beet | 416.2 g | LS2 from beet | 373.1 g |
| vinasse | 118.1 g | vinasse | 572.9 g |
| urea | 1.6 g | urea | 1.6 g |
| MgSO$_4$ 7H$_2$O at 9.5% | 0.1 g | MgSO$_4$ 7H$_2$O at 9.5% | 0.1 g |
| H$_3$PO$_4$ at 75% | 0.5 g | H$_3$PO$_4$ at 75% | 0.5 g |
| water initial pH 5 | q.s. 1 kg | Ammonium difluoride at 3.5% | 1.4 g |
| | | water initial pH 5 | q.s. 1 kg |

-continued

| Medium C | | Medium D | |
|---|---|---|---|
| Beet molasses | 394.7 g | Cane molasses | 315.2 g |
| (NH$_4$)$_2$HPO$_4$ | 4.7 g | glucose | 68.4 g |
| vitamins | | (NH$_4$)$_2$HPO$_4$ | 4.7 g |
| water | q.s. 1 kg | vitamins | |
| initial pH 5.3 | | water | q.s. 1 kg |
| | | initial pH 5.3 | |

| Medium E | |
|---|---|
| LS2 from beet | 353.1 g |
| vinasse | 413.2 g |
| urea | 0.39 g |
| (NH$_4$)$_2$HPO$_4$ | 0.13 g |
| Magnesium and zinc | |
| Process water* | 233.6 g |
| initial pH 5 | |

*mixture comprising water from the purification cycles, condensates from fermentation and from distillation Medium A contains 9% of non-sugars (relative to the total dry matter of the medium), the non-sugars being supplied by vinasse for the most part.

Medium B contains 9% of non-sugars (relative to the total dry matter of the medium), the non-sugars being supplied by vinasse for the most part.

Medium C contains 10.8% of non-sugars (relative to the total dry matter of the medium), the non-sugars being supplied by slightly diluted beet molasses (LS3).

Medium D contains 10.8% of non-sugars (relative to the total dry matter of the medium), the non-sugars being supplied by slightly diluted cane molasses (LS3).

Medium E contains 11% of non-sugars (relative to the total dry matter of the medium), the non-sugars being supplied by vinasse for the most part.

2. Fermentation and Measurement of Alcohol

The fermentation conditions are the same as in example 1, except that the fermentation medium contains sugar in a non-limiting amount.

The amount of alcohol produced is measured from the weight loss, as detailed in example 1.

Results

The hybrids 1 and 2 selected, corresponding respectively to yeast strains I-4264 and I-4265, are then tested in toxic application media.

The toxic application media tested are as follows:
media A and B containing a large amount of vinasse, and
media C and D containing slightly diluted molasses, from beet and cane respectively.

Clones A and C, corresponding respectively to yeast strains I-4411 and I-4412, are tested in toxic application medium E.

FIGS. 5 to 8 show the kinetics of alcohol production of yeast strains I-4264 and I-4265 according to the invention and of the reference strain I-4071, in media A, B, C and D respectively.

FIG. 9 shows the kinetics of alcohol production of yeast strains I-4411 and I-4412 and of the reference strain I-4071 in toxic application medium E.

Figure 5:
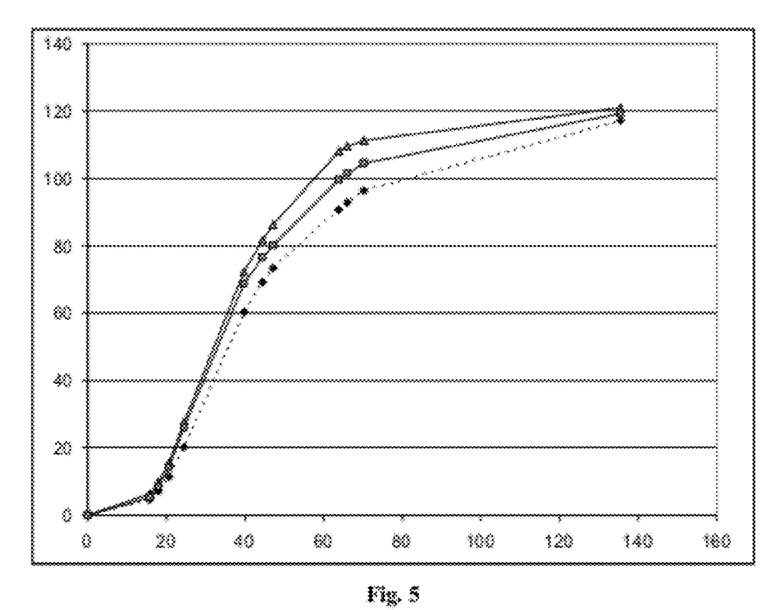
FIG. 5: Kinetics of alcohol production in fermentation in a toxic application medium A containing vinasse (sugar fermentation non-limiting)

As shown in FIG. 5, the kinetics of alcohol production of yeast strains I-4264 and I-4265 according to the invention is quicker than that of the reference strain I-4071 after 20 h of fermentation. The difference between the amount of alcohol produced by the hybrids and the amount of alcohol produced by the reference strain is accentuated from 20 h up to the end of fermentation.

As shown in FIG. 6, the kinetics of alcohol production of yeast strains I-4264 and I-4265 is quicker than that of the reference strain I-4071, after 20 h of fermentation and after 30 hours of fermentation, respectively. The lag phase of strain I-4264 is very short compared to the other 2 strains. The difference between the amount of alcohol produced by the hybrids and the amount of alcohol produced by the reference strain is accentuated from 20 h and 30 h respectively up to the end of fermentation.

As shown in FIGS. 7 and 8, the kinetics of alcohol production of yeast strains I-4264 and I-4265 is quicker than that of the reference strain I-4071 throughout the fermentation.

As shown in FIG. 9, the kinetics of alcohol production of yeast strains I-4411 and I-4412 is quicker than that of the reference strain I-4071 throughout the fermentation in application medium E.

In conclusion, reference strain I-4071 is more affected by the toxicity of the application media tested than yeast strains I-4264, I-4265, I-4411 and I-4412 according to the invention.

Yeast strains I-4264, I-4265, I-4411 and I-4412 according to the invention provide a kinetic advantage for alcohol production in toxic media.

The invention claimed is:

1. A method of selecting a yeast strain that is resistant to a toxic medium, comprising the steps of:
   fermenting at least one yeast strain in a toxic selective medium and in a non-toxic selective medium,
      wherein the initial composition of the toxic selective medium is the initial composition of the non-toxic selective medium with addition of at least one non-ionized organic acid at a concentration that has a toxic effect on alcohol production by the yeast strain deposited on Sep. 4, 2008 at the CNCM under number I-4071, and
      wherein sugar is the limiting factor of the fermentation in the toxic selective medium and in the non-toxic selective medium; and
   selecting at least one yeast strain for which the amount of alcohol produced at time $t_{max}$ in the toxic selective medium is greater than or equal to 65% of the amount of alcohol produced at time $t_{max}$ by said strain in the non-toxic selective medium, wherein $t_{max}$ is the time after fermentation initiation when the maximum amount of alcohol is produced by the yeast strain in the non-toxic selective medium.

2. The method according to claim 1, wherein the non-ionized organic acid is selected from acetic acid, lactic acid, formic acid, levulinic acid or a mixture thereof.

3. The method according to claim 1, wherein the toxic selective medium and the non-toxic selective medium are synthetic media.

4. The method according to claim 1, further comprising an additional step of selection of at least one yeast strain for which the amount of alcohol produced at time $t_{max\ ref}$ in said toxic selective medium is greater than the amount of alcohol produced at time $t_{max\ ref}$ by yeast strain number I-4071 in said same toxic selective medium, wherein $t_{max\ ref}$ is the time after fermentation initiation when the maximum amount of alcohol is produced by yeast strain number I-4071 in the non-toxic selective medium.

5. The method according to claim 1, further comprising an additional step of selection, in a non-toxic selective medium in which sugar is not the limiting factor of fermentation, of at least one yeast strain for which the maximum amount of alcohol produced is greater than or equal to 90% of the maximum amount of alcohol produced by strain number I-4071 in said same non-toxic selective medium.

6. The method according to claim 1, further comprising a prior step of obtaining yeast strains by crossing and/or mutagenesis.

* * * * *